US012810991B2

(12) United States Patent
Lee

(10) Patent No.: US 12,810,991 B2
(45) Date of Patent: Nov. 24, 2026

(54) METHOD AND SYSTEM FOR ANALYZING INGREDIENT INDEX AND FOOD MATERIAL USING MEDICAL DATA BASED ON ARTIFICIAL INTELLIGENCE

(71) Applicant: MEDIFOODPLATFORM CO., LTD., Seoul (KR)

(72) Inventor: Kiho Lee, Seoul (KR)

(73) Assignee: MEDIFOODPLATFORM CO., LTD., Seoul (KR)

( * ) Notice: Subject to any disclaimer, the term of this patent is extended or adjusted under 35 U.S.C. 154(b) by 810 days.

(21) Appl. No.: 18/347,849

(22) Filed: Jul. 6, 2023

(65) Prior Publication Data

US 2023/0360771 A1 Nov. 9, 2023

Related U.S. Application Data

(63) Continuation-in-part of application No. PCT/KR2022/002768, filed on Feb. 25, 2022.

(30) Foreign Application Priority Data

Feb. 22, 2022 (KR) ........................ 10-2022-0023238

(51) Int. Cl.

| | |
|---|---|
| ***G16H 20/60*** | (2018.01) |
| ***G06N 5/022*** | (2023.01) |
| ***G16B 50/00*** | (2019.01) |
| ***G16H 70/00*** | (2018.01) |
| ***G16H 80/00*** | (2018.01) |

(52) U.S. Cl.

CPC ............. *G16H 20/60* (2018.01); *G06N 5/022* (2013.01); *G16B 50/00* (2019.02); *G16H 70/00* (2018.01); *G16H 80/00* (2018.01)

(58) Field of Classification Search

None

See application file for complete search history.

(56) References Cited

U.S. PATENT DOCUMENTS

| | | | | |
|---|---|---|---|---|
| 10,825,567 | B1 | 11/2020 | Wala et al. | |
| 11,037,681 | B1 * | 6/2021 | Wala | G16H 20/60 |

(Continued)

FOREIGN PATENT DOCUMENTS

| | | | |
|---|---|---|---|
| CN | 112071396 | A | 12/2020 |
| CN | 112071398 | A | 12/2020 |

(Continued)

OTHER PUBLICATIONS

U.S. Department of Health and Human Services, Food and Drug Administration, Center for Food Safety and Applied Nutrition, “Frequently Asked Questions About Medical Foods”; Third Edition: Guidance for Industry, 12 pages (Year: 2023).*

(Continued)

*Primary Examiner* — Michael Fuelling

(74) *Attorney, Agent, or Firm* — Studebaker Brackett PLLC

(57) ABSTRACT

The present disclosure relates to an artificial intelligence-based food material analyzing method, which can calculate ingredient power for an inspection item of each ingredient, calculate an ingredient index the sum of ingredient powers for test items with respect to each ingredient, and derive a food material optimized for a living thing on the basis of the calculated ingredient index.

14 Claims, 11 Drawing Sheets

(56) References Cited

U.S. PATENT DOCUMENTS

| | | | | |
|---|---|---|---|---|
| 11,688,506 | B2 * | 6/2023 | Neumann | G16H 10/20<br>705/2 |
| 12,046,350 | B2 * | 7/2024 | Neumann | G16H 10/20 |
| 2013/0295531 | A1 | 11/2013 | Addanki et al. | |
| 2015/0279235 | A1 | 10/2015 | Yamada | |
| 2021/0343393 | A1 | 11/2021 | Nakamura | |
| 2022/0036997 | A1 * | 2/2022 | Neumann | G16H 20/60 |
| 2022/0036998 | A1 * | 2/2022 | Neumann | G16H 20/60 |
| 2022/0262495 | A1 * | 8/2022 | Kanda | G16H 50/30 |
| 2023/0274812 | A1 * | 8/2023 | Neumann | G16H 20/60<br>705/2 |
| 2024/0087719 | A1 * | 3/2024 | Neumann | G16H 20/60 |
| 2024/0363224 | A1 * | 10/2024 | Neumann | G06N 20/00 |
| 2025/0182877 | A1 * | 6/2025 | Kanda | G16H 50/30 |

FOREIGN PATENT DOCUMENTS

| | | | |
|---|---|---|---|
| CN | 112493522 | A | 3/2021 |
| JP | 2015-194807 | A | 11/2015 |
| KR | 10-2011836 | B1 | 8/2019 |
| KR | 10-2020-0098155 | A | 8/2020 |
| KR | 10-2186267 | B1 | 12/2020 |
| KR | 10-2289256 | B1 | 8/2021 |
| KR | 10-2360651 | B1 | 2/2022 |

OTHER PUBLICATIONS

Yu-Lun Hsieh et al., “Social Media Mining for an Analysis of Nutrition and Dietary Health in Taiwan.” Nutrients 2021, 13, 1778; May 23, 2021; pp. 1-19.

International Search Report issued in PCT/KR2022/002768; mailed Nov. 16, 2022.

* cited by examiner

METHOD AND SYSTEM FOR ANALYZING INGREDIENT INDEX AND FOOD MATERIAL USING MEDICAL DATA BASED ON ARTIFICIAL INTELLIGENCE

CROSS-REFERENCE TO RELATED APPLICATION

The present application is a continuation-in-part application of International Patent Application No. PCT/KR2022/002768, filed on Feb. 25, 2022, which is based upon and claims the benefit of priority to Korean Patent Application No. 10-2022-0023238, filed on Feb. 22, 2022. The disclosures of the above-listed applications are hereby incorporated by reference herein in their entirety.

BACKGROUND

Technical Field

The present disclosure relates to an artificial intelligence-based food material analyzing method.

Description of Related Art

Most drugs prescribed to a target individual who has a specific disease or to a target individual who requires improvement in terms of physical condition originate from herbal medicines or living things.

In the case of providing a diet by analyzing food materials optimized for the above-described target individual using the above, it is expected that the disease can be quickly improved, or the target individual's physical condition can rapidly improve.

However, due to the nature of modern medical science, there are several disadvantages in that even a doctor may lack medical knowledge in fields other than the doctor's specialization and in that it is too difficult to know all of the vast amount of knowledge related to food materials.

On the contrary, in the case of a person having vast knowledge of food materials and nutrients, it is difficult to have medical knowledge on the level of that of a doctor.

If the physical conditions of living things are accurately analyzed and suitable ingredients are provided, it is expected to improve the physical conditions of living things or to mitigate the effects of a disease. However, such a technology currently does not exist due to the above disadvantages.

SUMMARY

The present disclosure has been made to solve the above-mentioned problems occurring in the prior art, and an aspect of the present disclosure is directed to providing an artificial intelligence-based food material analyzing method.

Another aspect of the present disclosure is directed to calculating ingredient power for each inspection item, calculating the ingredient index, the sum of the ingredient powers for the inspection items of each ingredient, and deriving food materials for living things based on the calculated ingredient index.

The aspects of the present disclosure are not limited to those mentioned above, and other aspects not mentioned herein will be clearly understood by those skilled in the art from the following description.

To accomplish the above objects, in an aspect of the present disclosure, there is provided an artificial intelligence-based food material analyzing method including the operations of: receiving, by a client terminal device, user information of a user; transmitting, by the client terminal device, to a service server device, the user information; requesting, by the service server device, to a medical staff terminal device, medical data corresponding to the user information; retrieving, by the medical staff terminal device, in a medical database, the medical data corresponding to the user information, wherein the medical data include information on inspection items and a plurality of hierarchy levels of the inspection items corresponding to the user information; transmitting, by the medical staff terminal device, the medical data to the service server device; generating, by the service server device, analysis input data including the user information and the medical data; inputting, by the service server device, the analysis input data to an artificial intelligence-based algorithm stored in a memory of the service server device, wherein the artificial intelligence-based algorithm performs: calculating ingredient power for each inspection item of the inspection items with respect to a first ingredient; calculating a first ingredient index that is a sum of ingredient powers for test items with respect to the first ingredient; deriving food material information based on the first ingredient index, from the food material database arranged based on ingredient contents; and outputting the derived food material information as a result value; and transmitting, from the service server device, the derived food material information to the client terminal device; and accessing, by the client terminal device, food material storage information, which indicates amounts of food materials stored in a food material storage of the user, and checking, by the client terminal device, whether an amount of an ingredient corresponding to the derived food material information, in the food material storage, exceeds a threshold level; in response to a detection that the amount of an ingredient corresponding to the derived food material information, in the food material storage, does not exceed the threshold level, generating and transmitting, by the client terminal device, a grocery order signal to a grocery delivery service server, wherein the calculating the ingredient power comprises: calculating a first weighted value corresponding to an importance of the inspection item, wherein the importance of the inspection item is based on a hierarchy level corresponding to the inspection item; calculating a second weighted value corresponding to a result value of the inspection item, wherein the result value is based on an input value of the inspection item for the user; calculating a third weighted value based on the second weighted value, wherein the third weighted value is based on output data of the inspection item for the user; and calculating the ingredient power by multiplying the first weighted value, the second weighted value, and the third weighted value.

Further, the method may further include: calculating ingredient power for each inspection item with respect to a first ingredient; calculating a first ingredient index, the sum of ingredient powers for test items with respect to the first ingredient; and deriving at least one food material on the basis of the first ingredient index, wherein the ingredient power calculating operation comprises the operations of: calculating a first weighted value corresponding to the importance of the inspection item; calculating a second weighted value corresponding to a result value of the inspection item; calculating a third weighted value based on the second weighted value; and calculating the ingredient power by multiplying the first weighted value, the second weighted value, and the third weighted value.

Moreover, the second weighted value calculating operation is to calculate the second weighted value according to the importance of an inspection result with respect to each inspection item based on the result value.

Furthermore, the third weighted value is to increase, reduce, or invalidate the influence of the second weighted value by a particular coefficient. The third weighted value calculating operation is to calculate the third weighted value based on a type of the corresponding inspection item and the second weighted value calculated with respect to the corresponding inspection item.

Additionally, the third weighted value is a weighted value for the efficacy of the analysis object of the first ingredient according to the result value of the inspection item. The third weighted value calculating operation is to calculate the third weighted value on the basis of the type of the first ingredient, the type of the corresponding inspection item, and the result value of the corresponding inspection item.

In addition, the inspection item includes at least one upper classification item, and a service server calculates the first weighted value by multiplying a classification weighted value set for at least one upper classification item to which the inspection item belongs.

Moreover, the food material deriving operation includes the operations of: correcting the calculated first ingredient index; setting the number of food material data extractions on the basis of the corrected first ingredient index; extracting as many food materials as the set food material data extraction number; calculating scores of food materials by adding at least one first ingredient index corresponding to each extracted food material; and providing a necessary intake amount of each food material on the basis of the score of each calculated food material.

Furthermore, after the food material deriving operation, the method further includes a food material post-processing operation of deriving the final food material information by performing at least one of filtering the derived food material and deriving a substitutional food material.

Additionally, after the food material deriving operation, the method further includes: analyzing food corresponding to the derived final food material information; and providing a menu based on the analyzed food.

In another aspect of the present disclosure, there is provided an artificial intelligence-based food material analyzing server including: a memory storing a weighted value calculation algorithm; and a processor which calculates ingredient power which calculates ingredient power for each inspection item with respect to a first ingredient, calculates a first ingredient index the sum of ingredient powers for test items with respect to the first ingredient, and derives at least one food material on the basis of the first ingredient index, wherein the processor calculates a first weighted value corresponding to the importance of the inspection item, calculates a second weighted value corresponding to a result value of the inspection item, calculates a third weighted value based on the second weighted value, and calculates the ingredient power by multiplying the first weighted value, the second weighted value, and the third weighted value.

Besides the above, other methods and systems for embodying the present disclosure and a computer readable recording medium to record computer program for executing the method may be additionally provided.

According to the present disclosure, an artificial intelligence-based food material analyzing method can be provided.

According to the present disclosure, ingredient power for each inspection item can be calculated, the ingredient index, the sum of the ingredient powers for the inspection items of each ingredient, can be calculated, and then, food materials for living things can be derived based on the calculated ingredient index.

The advantages of the present disclosure are not limited to the above-mentioned advantages, and other advantages, which are not specifically mentioned herein, will be clearly understood by those skilled in the art from the following description.

DETAILED DESCRIPTION

Advantages and features of the present disclosure and methods accomplishing the advantages and features will become apparent from the following detailed description of exemplary embodiments with reference to the accompanying drawings. However, the present disclosure is not limited to exemplary embodiment disclosed herein but will be implemented in various forms. The exemplary embodiments are provided so that the present disclosure is completely disclosed, and a person of ordinary skilled in the art can fully understand the scope of the present disclosure. Therefore, the present disclosure will be defined only by the scope of the appended claims.

Terms used in the specification are used to describe specific embodiments of the present disclosure and are not intended to limit the scope of the present disclosure. In the specification, the terms of a singular form may include plural forms unless otherwise specified. It should be also understood that the terms of 'include' or 'have' in the specification are used to mean that there is no intent to exclude existence or addition of other components besides components described in the specification. In the detailed description, the same reference numbers of the drawings refer to the same or equivalent parts of the present disclosure, and the term "and/or" is understood to include a combination of one or more of components described above. It will be understood that terms, such as "first" or "second" may be used in the specification to describe various components but are not restricted to the above terms. The terms may be used to discriminate one component from another component. Therefore, of course, the first component may be named as the second component within the scope of the present disclosure.

Unless otherwise defined, all terms (including technical and scientific terms) used herein have the same meaning as commonly understood by those skilled in the technical field to which the present disclosure pertains. It will be further understood that terms, such as those defined in commonly used dictionaries, should not be interpreted in an idealized or overly formal sense unless expressly so defined herein.

Hereinafter, preferred embodiments of the present disclosure will be described in detail with reference to the accompanying drawings.

Figure 1:
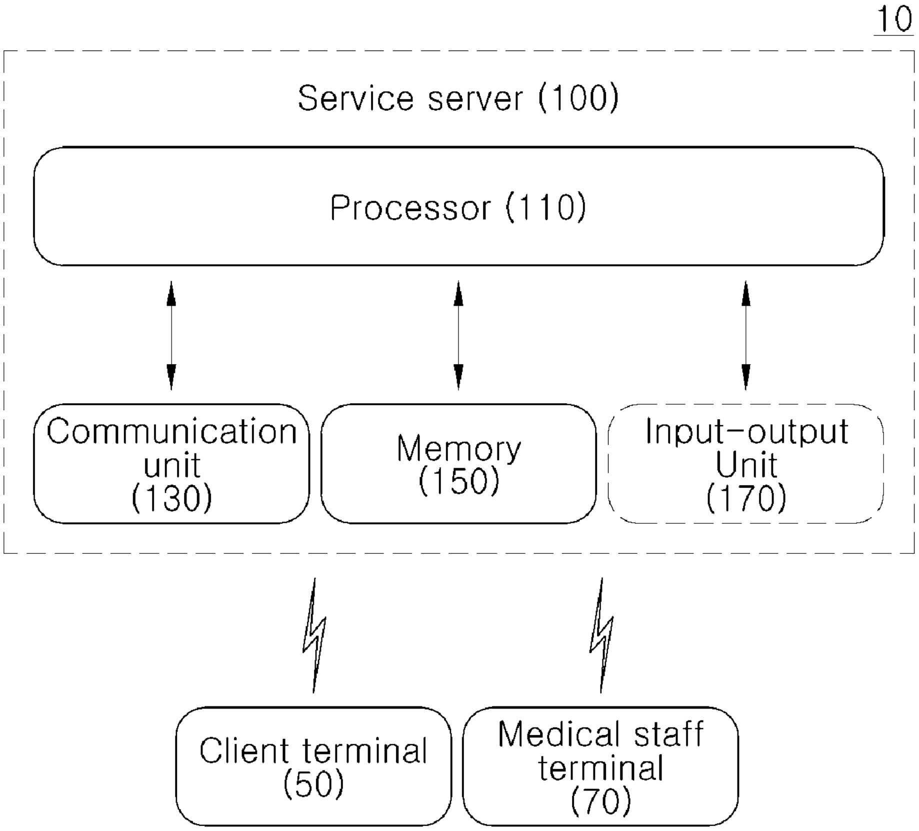
FIG. 1 is a block diagram of an artificial intelligence-based food material analyzing system according to an embodiment of the present disclosure.

FIG. 1 is a block diagram of an artificial intelligence-based food material analyzing system 10 according to an embodiment of the present disclosure.

The artificial intelligence-based food material analyzing system 10 according to the embodiment of the present disclosure includes a service server 100, a client terminal 50, and a medical staff terminal 70.

The service server 100 includes a processor 110, a communication unit 130, a memory 150, and an input-output unit 170.

However, in several embodiments, the food material analyzing system 10 or the service server 100 may include more or less components than the components illustrated in FIG. 1.

The artificial intelligence-based food material analyzing system according to the embodiment of the present disclosure may include a service server 100 of an artificial intelligence-based food material analyzing server having a server device as illustrated in FIG. 1.

The artificial intelligence-based food material analyzing server according to the embodiment of the present disclosure creates and outputs output data according to an internal algorithm and a process when input data for an analysis object is inputted.

In this instance, it is possible to apply any of the analysis objects.

As a representative example, the analysis object may be a patient who has a specific disease or a person who needs improvement of a physical condition. However, the analysis object is not limited thereto, and may be a pet, an animal in a zoo, or a plant.

Therefore, the patient, the person, the pet, the animal, or the plant is referred to as an analysis object.

The communication unit 130 can communicate with at least one of the client terminal 50 and the medical staff terminal 70, receive input data for an artificial intelligence-based food material analyzing service, and provide the created result data to the client terminal 50.

The client terminal 50 is a device for requesting analysis of an analysis object to the service server 100, and any information processing means, such as a computer, a smart phone, a tablet PC, or the like, can be applied.

Moreover, as described above, the analysis object requested to be analyzed from the client terminal 50 may be a client, but may be a family member or an acquaintance of the client, an animal, a plant, or the like.

The medical staff terminal 70 provides medical data for an analysis object to the service server 100, and various examples such as a terminal of a doctor, a terminal of a medical staff, a hospital server, and the like, are applicable as the medical staff terminal.

In several embodiments, the service server 100 can access a server of an affiliated medical institution to receive medical data for the analysis object when a food material analyzing service request for the analysis object is received from the client terminal 50, and automatically input the medical data to an algorithm and output a result value.

The service server 100 can provide an artificial intelligence-based food material analyzing service through a service application or a web.

The memory 150 may store a weight calculation algorithm, an artificial intelligence model, a food material analyzing history of an analysis object, and the like.

Furthermore, the memory 150 stores various commands, algorithms, and the likes for providing the artificial intelligence-based food material analyzing service according to an embodiment of the present disclosure.

The input-output unit 170 can directly input a control signal to the service server 100 or output information on a created result, an analyzed result, or the like.

In several embodiments, the input-output unit 170 may be used by an administrator of the service server 100, and may be utilized to output inspection results for checking an algorithm, a firmware update, and an error.

The processor 110 controls operations of components in the service server 100, and provides an artificial intelligence-based food material analyzing method according to an embodiment of the present disclosure by using commands, algorithms, and artificial intelligence models stored in the memory 150.

Hereinafter, referring to the flow chart of FIG. 2 and other exemplary views, artificial intelligence-based food material analyzing server and method according to an embodiment of the present disclosure will be described in more detail.

Figure 2:
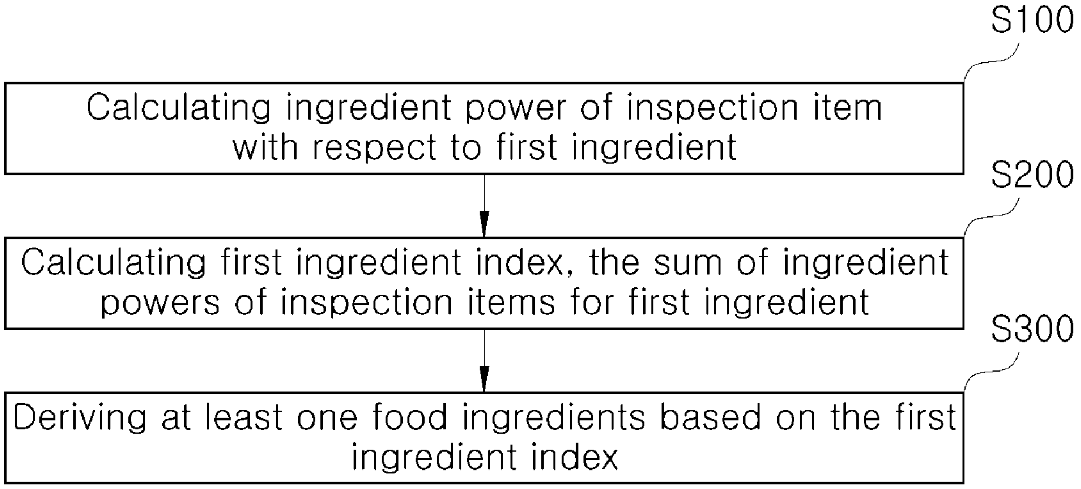
FIG. 2 is a flow chart of an artificial intelligence-based food material analyzing method according to an embodiment of the present disclosure.

FIG. 2 is a flow chart of an artificial intelligence-based food material analyzing method according to an embodiment of the present disclosure.

Figure 3:
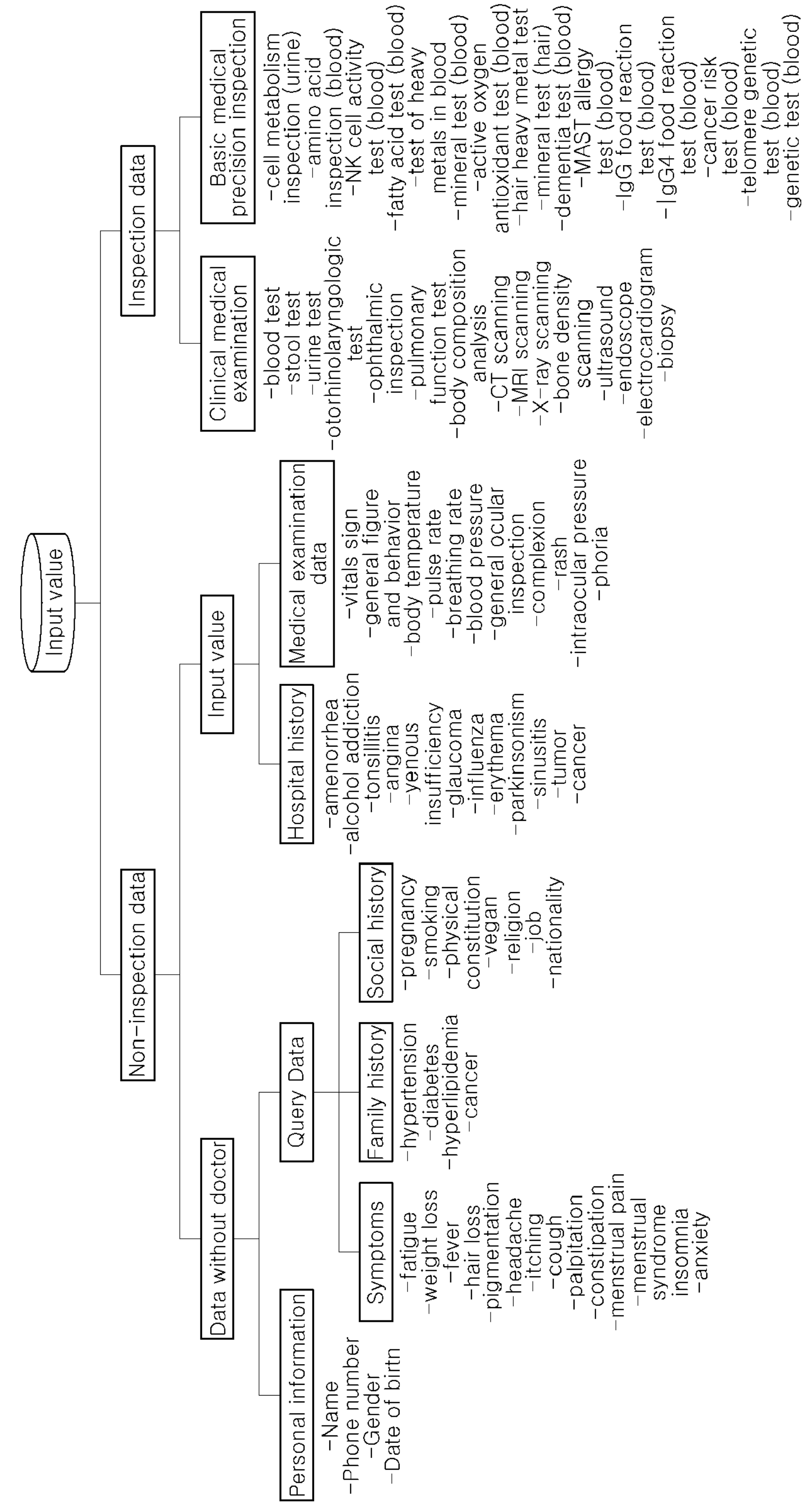
FIGS. 3 and 4 are views illustrating types of inspection items.
Figure 4:
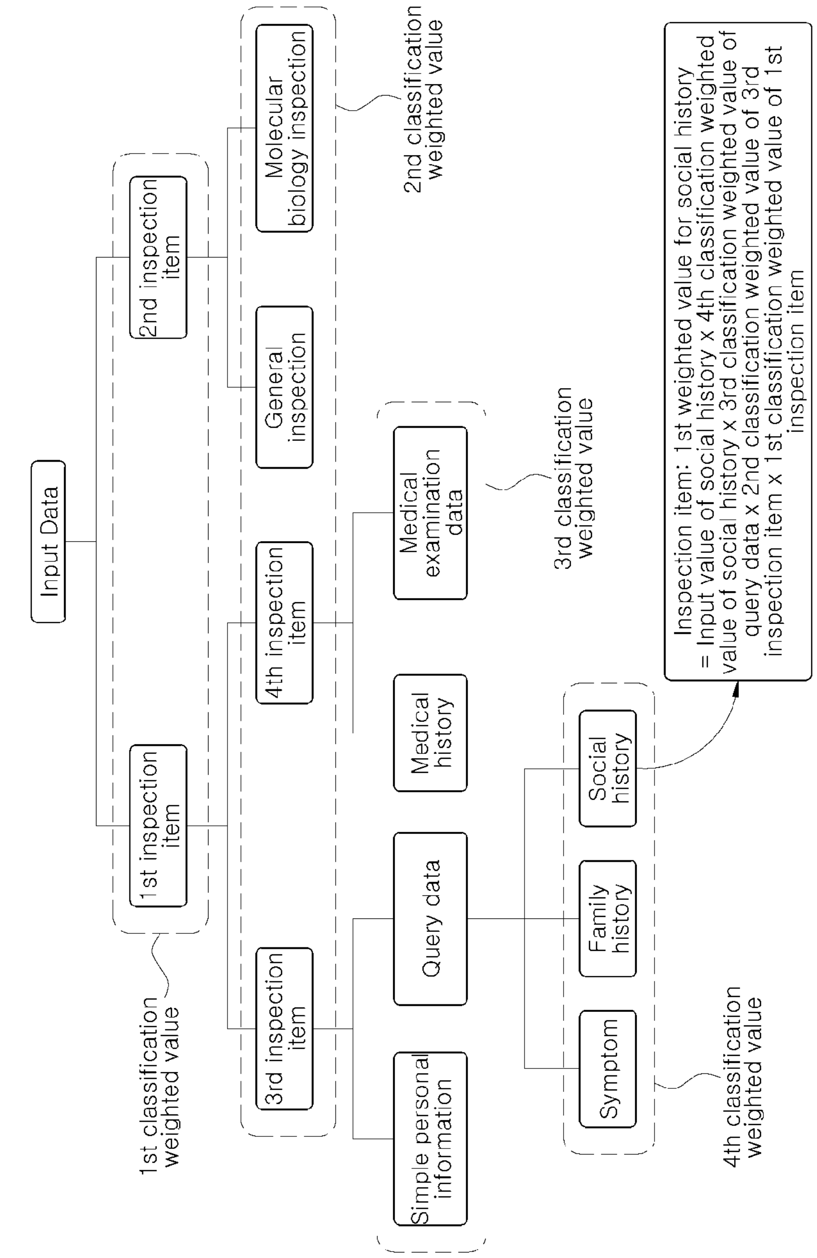

FIGS. 3 and 4 illustrate types of inspection items.

The processor 110 calculates ingredient power for each inspection item with respect to the first ingredient (S100).

The processor 110 calculates the first ingredient power index the sum of ingredient powers for inspection items with respect to the first ingredient (S200).

The processor 110 derives at least one food material based on the first ingredient index (S300).

The artificial intelligence-based food material analyzing server according to the embodiment of the present disclosure calculates ingredient powers for inspection items with respect to various ingredients.

The first ingredient refers to one of various ingredients, such as calcium, magnesium, copper, vitamin, omega 3 fatty acid, methionine, tryptophan, selenium, zinc, gluten, etc. Finally, the service server 100 analyzes an analysis object and performs analysis on all ingredients to provide the optimized food material.

The processor 110 calculates ingredient power for each inspection item with respect to a specific ingredient through the operation (S100), and calculates an ingredient index by summing the calculated ingredient powers for all inspection items of the corresponding ingredient.

That is, according to result values by an input value of an analysis object for each inspection item, ingredient power to show which ingredients or how many ingredients are required to an analysis object is calculated. In this instance, one ingredient does not correspond to only one inspection item, but may correspond to a plurality of inspection items.

For example, if the ingredient power of vitamin C in the first inspection item is calculated as 10 with respect to the analysis object and the ingredient power in the second inspection item is calculated as 20, it means that vitamin C is an important ingredient to the analysis object. Therefore, 30, the sum of 10 and 20 is calculated as the ingredient index.

When calculation of the ingredient index calculation, the sum of the ingredient powers for all ingredients, is completed through the operations (S100 and S200), the processor 110 proceeds to an operation (S300) to derive at least one food material for the analysis object on the basis of the ingredient index calculated with respect to all components.

FIG. 3 illustrates types of inspection items. The inspection items include at least one upper classification item, and in the classification items of FIG. 3, the lowest classification item list means each inspection item.

In an embodiment of the present disclosure, the highest rank inspection item includes inspection data items and non-inspection data items.

The inspection data item (second inspection item) includes inspection items requiring medical examination, and includes general examination (clinical medical examination) and molecular biology inspection (basic medical precision inspection).

Referring to FIG. 3, the general examination (clinical medical examination) includes at least one among a blood test, a stool test, a urine test, an otorhinolaryngologic test, an ophthalmic inspection, a pulmonary function inspection, a body composition analysis, a CT scanning, an MRI scanning, an X-ray scanning, a bone density scanning, an ultrasound, an endoscope, an electrocardiogram, and a biopsy, and may include any of inspection items corresponding to general inspection (clinical medical examination) in addition to that shown in FIG. 3.

Referring to FIG. 3, molecular biology inspection (basic medical precision inspection) includes at least one among a cell metabolism inspection (urine), an amino acid inspection (blood), an NK cell activity test (blood), a fatty acid test (blood), a test of heavy metals in blood, a mineral test (blood), an active oxygen antioxidant test (blood), a hair heavy metal test, a mineral test (hair), a dementia test (blood), an MAST allergy test (blood), an IgG food reaction test (blood), an IgG4 food reaction test (blood), a cancer risk test (blood), a telomere genetic test (blood), and a genetic test (blood), and may include any of inspection items corresponding to molecular biology inspection (basic medical precision inspection) in addition to that shown in FIG. 3.

The non-inspection data item includes inspection items that do not require medical examination.

However, that does not require medical examination does not mean that a client or an analysis object can directly input inspection items included in the non-inspection data item.

In detail, the non-inspection data item is classified into a data item (a third inspection item) that a client can directly input without a doctor, and a data item (a fourth inspection item) that a client can input through a doctor.

In this instance, the data item (fourth inspection item) through the doctor can mean data requiring determination/diagnosis of the doctor.

The data item (fourth inspection item) through the doctor can be classified into a hospital history item and group history item and a medical examination data item (physical examination).

Referring to FIG. 3, the hospital history item includes at least one among amenorrhea, alcohol addiction, tonsillitis, angina, venous insufficiency, glaucoma, influenza, erythema, parkinsonism, sinusitis, tumor, and cancer, and may include any of inspection items corresponding to the hospital history item in addition to that shown in FIG. 3.

Referring to FIG. 3, the medical examination data item means an inspection item requiring physical examination, and includes at least one among vital signs, general figures and behaviors, body temperature, a pulse rate, a breathing rate, blood pressure, general ocular inspection, complexion, rash, intraocular pressure, and phoria of an analysis object, and may include any of inspection items corresponding to the medical examination data item in addition to that shown in FIG. 3.

The data item without a doctor (third inspection item) may include a simple personal information item of an analysis object and a query data item for the analysis object.

Referring to FIG. 3, the simple personal information item includes at least one among name, phone number, gender, and date of birth of the analysis object, and may include any of inspection items corresponding to the simple personal information item in addition to that shown in FIG. 3.

The query data item may include a symptom item, a family history item, and a social history item.

The symptom item includes at least one among fatigue, weight loss, fever, hair loss, pigmentation, headache, itching, cough, palpitation, constipation, menstrual pain, menstrual syndrome, insomnia, and anxiety, and may include any of inspection items corresponding to the symptom item in addition to that shown in FIG. 3.

The family history item includes at least one among hypertension, diabetes, hyperlipidemia, and cancer, and may include any of the inspection items corresponding to the family history item in addition to that shown in FIG. 3.

The social history item includes at least one among pregnancy, smoking, physical constitution, vegan, religion, job, and nationality, and may include any of inspection items corresponding to the social history item in addition to that shown in FIG. 3.

The artificial intelligence-based food material analyzing method according to an embodiment of the present disclosure derives food materials on the basis of input data for each inspection item with respect to the analysis object, but does not use them as they are. The artificial intelligence-based food material analyzing method applies various weighted values to derive a result optimized for the analysis object.

An embodiment of the weighted value calculation will be described in detail below.

Figure 5:
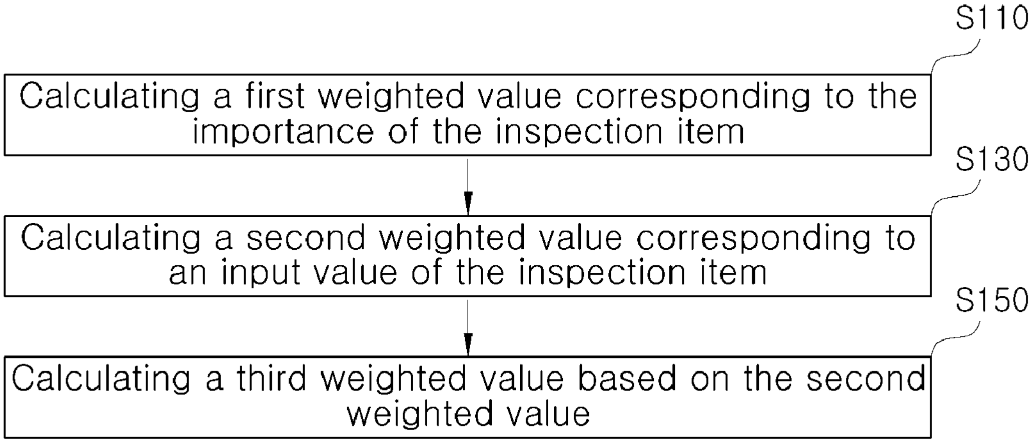
FIG. 5 is a detailed flow chart of ingredient power calculating operation.

FIG. 5 is a detailed flow chart of the ingredient power calculating operation (S100).

Referring to FIG. 5, the ingredient power calculating operation (S100) includes the following operations.

The processor 110 calculates a first weighted value corresponding to the importance of each item of the inspection item (S110).

With reference to FIGS. 3 and 4, various inspection items are described, and it is found that the importance is different in each category to which the inspection item belongs.

The first weighted value is a category weighted value and means a weighted value to which diagnostic reliability for each inspection method is reflected.

For instance, the inspection data item may have a weighted value higher than the non-inspection data item and the data item through a doctor (fourth inspection item), or the non-inspection data item and the data item through a doctor (fourth inspection item) may have a weighted value higher than the data item without a doctor (third inspection item).

However, the above is just an example, but the present disclosure is not limited thereto.

As described above, with reference to FIGS. 3 and 4, the inspection item includes at least one upper classification item.

A classification weighted value is set to each classification item.

Referring to FIG. 4, the first classification weighted value is set to the first inspection item (first classification weighted value) and the second inspection item (second classification weighted value).

In one embodiment, the second classification weighted value is set to the third inspection item (2-1 classification weighted value), the fourth inspection item (2-2 classification weighted value), the general inspection item (2-3 classification weighted value), and the molecular biology inspection item (2-4 classification weighted value).

In one embodiment, the third classification weighted value is set to the simple personal information item (3-1 classification weighted value), the query data item (3-2 classification weighted value), the hospital history item (3-3 classification weighted value), and the medical examination data item (3-4 classification weighted value).

In one embodiment, the fourth classification weighted value is set to the symptom item (4-1 classification weighted value), the family history item (4-2 classification weighted value), and the social history item (4-3 classification weighted value).

In one embodiment, the inspection item may include at least one upper classification item.

In addition, the processor 110 can calculate the first weighted value by multiplying the classification weighted value set for at least one upper classification item to which the inspection item belongs.

In more detail, the processor 110 can calculate the first weighted value by multiplying the classification weighted value set for all upper classification items to which the inspection items belong.

For instance, as shown in FIG. 4, the first weighted value for the social history can be calculated on the basis of a result value of the social history (the fourth classification weighted value of the social history) of the analysis object×the third classification weighted value of the query data×the second classification weighted value of the third inspection item× the first classification weighted value of the first inspection item.

In this instance, the fourth classification weighted value of the social history means a result value calculated on the basis of an input value of the corresponding inspection item of the analysis object.

In detail, the first weight for the social history can be calculated on the basis of the first classification weighted value×the 2-1 classification weighted value×the 3-2 classification weighted value×the result value of the social history (4-3 classification weighted value of the social history) of the analysis object.

The processor 110 calculates the second weighted value corresponding to the result value according to the input value of the inspection item (S130).

The second weighted value is a weighted value assigned according to the importance of the inspection result, and is assigned according to the numerical range of a data value, and the numerical range may be different depending on the types of data.

For example, an inspection item A may include four numerical ranges, an inspection item B may include five numerical ranges, and an inspection item C may include seven numerical ranges.

The second weighted value is not necessarily weighted, and minus, zero, and plus may be all applicable, and the numerical value of the decimal point is also applicable.

According to a first embodiment, the processor 110 can calculate the second weighted value so that a numerical inspection value (a result value output through an input value for an analysis object) is assigned according to the degree deviated from a preset reference value.

According to a second embodiment, the processor 110 can calculate the second weighted value so that an numerical inspection value (a result value output through an input value for an analysis object) is assigned by each grade, e.g., Very Low/Low/Mild or Very Deficient/a bit short in ingredient, etc.).

The processor 110 calculates the third weighted value on the basis of the second weighted value calculated in operation (S130). (S150)

The third weighted value may have the following purposes.

① The third weighted value may be to increase, reduce, or invalidate the influence of the second weighted value by a particular coefficient.

② The third weighted value may be for a weighted value for the inspection object of the first ingredient according to the result value (output data) of the inspection item.

The processor 110 can calculate the third weighted value on the basis of types of the corresponding inspection item and the second weighted value calculated with respect to the corresponding inspection item.

In more detail, it has been mentioned that the second weighted value with respect to the inspection item includes at least one numerical range.

Figure 6:
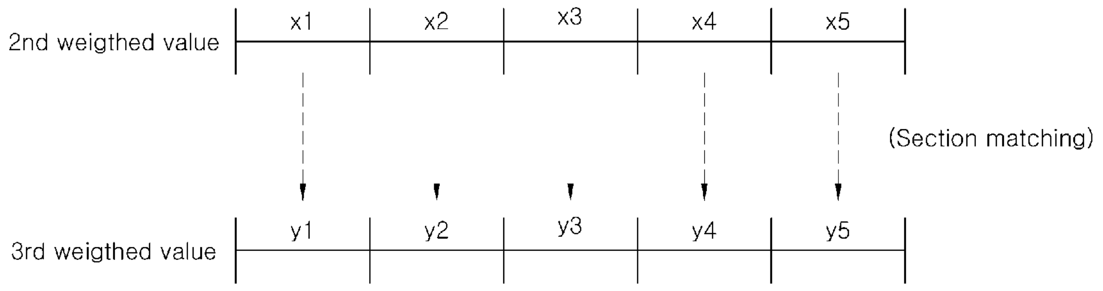
FIG. 6 is a view illustrating section matching of a second weighted value and a third weighted value.

FIG. 6 is a view illustrating section matching of the second weighted value and the third weighted value.

The processor 110 can calculate the third weighted value through section matching with the second weighted value when calculating the third weighted value.

The third weighted value with respect to the same inspection item may include a numerical range of the same number as the second weighted value.

It is to increase, reduce, or invalidate the influence of the second weighted value by a particular coefficient as described in the purpose ①.

For example, the second weighted value may be set to the first inspection item to have four numerical ranges of 0/0/1/5 according to the range of the result values.

In this case, the third weighted value of the first inspection item may be set to have four numerical ranges in the same way as the second weighted value.

However, the second weighted value and the third weighted value are the same in the number of numerical ranges, but the weighted values may be different from each other.

Figure 7:
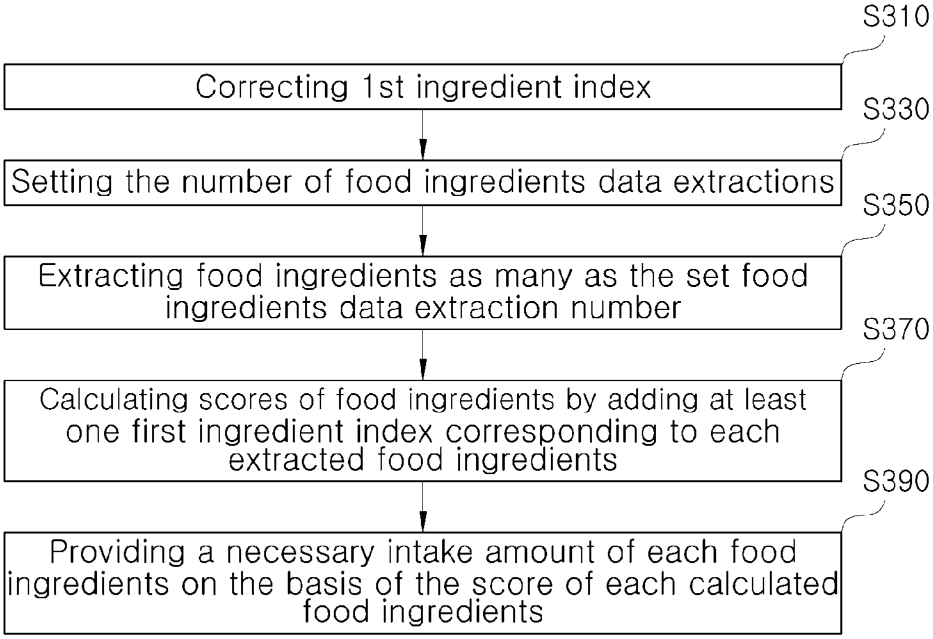
FIG. 7 is a detailed flow chart of a food material deriving operation.

FIG. 7 is a detailed flow chart of the food material deriving operation.

Figure 8:
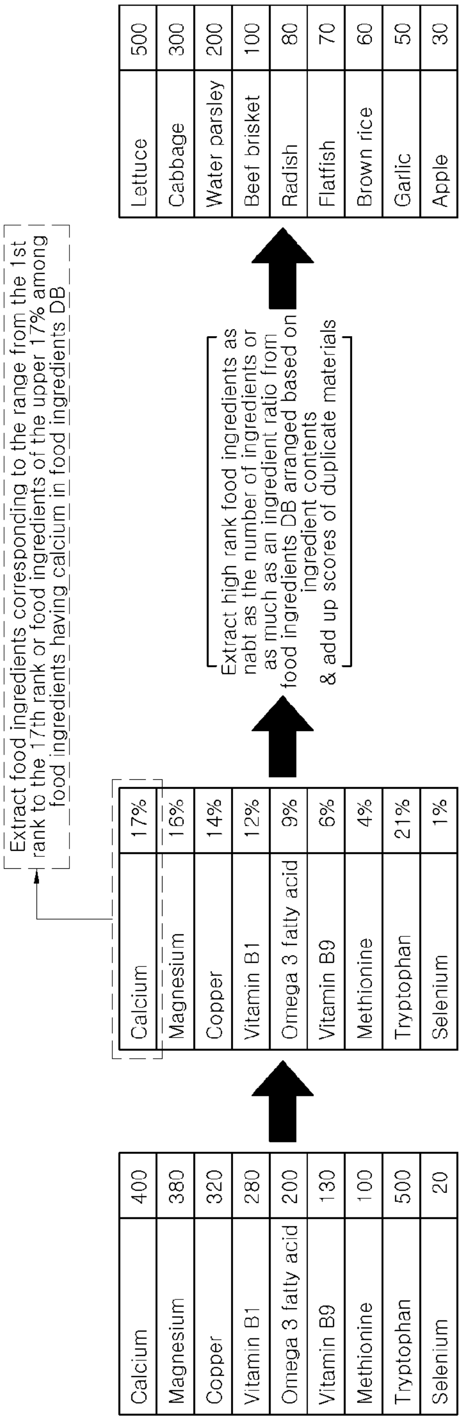
FIG. 8 is a view illustrating that high rank food materials are extracted as many as the number of ingredients or as much as an ingredient ratio from a food material database arranged based on ingredient contents.

FIG. 8 is a view illustrating that high rank food materials as many as the number of ingredients or as much as an ingredient ratio from a food material database arranged based on ingredient contents.

Referring to FIG. 7, the food material deriving operation includes the following operations.

The processor 110 corrects the first ingredient index calculated in the operation (S200). (S310)

In detail, the processor 110 can adjust the ingredient index by adjusting the ingredient index of all ingredients calculated in the operation (S200) by the percentile rank.

The processor 110 sets the number of food material data extractions. (S330)

The processor 110 extracts as many food materials as the food material data extraction number set in the operation (S330). (S350)

The processor 110 sets the food material data extraction number on the basis of the ingredient index corrected in the operation (S310), and the following embodiment can be applied.

① The processor 110 can extract the food material data as many as the number corresponding to the percentage of the corrected ingredient index.

Referring to FIG. 8, in the case of ①, the processor 110 may extract food materials corresponding to the range from the 1st rank to the 17th rank among food materials having calcium in the food material DB.

② The processor 110 can extract the food material data as many as the ratio corresponding to the percentage of the corrected ingredient index.

Referring to FIG. 8, in the case of ②, the processor 110 may extract food materials of the upper 17% among food materials having calcium in the food material DB.

The processor 110 calculates scores of food materials by adding the first ingredient index corresponding to the food materials extracted in the operation (S350). (S370)

For example, if the example illustrated in FIG. 8 is lettuce and the lettuce is extracted as the high rank food material in calcium ingredient and magnesium ingredient, the score of the lettuce may be calculated as 780 by summing the ingredient index (400) for calcium and the ingredient index (380) for magnesium.

According to an embodiment of the present disclosure, the processor 110 can assign a content weighted value for each food material.

In detail, the processor 110 can calculate a score for each food material by multiplying a content ratio with respect to a food material corresponding to the first rank ingredient index.

For instance, when five food materials including calcium have been extracted, and the first to fifth rank food materials respectively include 50 mg, 40 mg, 30 mg, 20 mg, 10 mg of calcium per 100 g, the processor 110 can calculate food material scores, namely, the score of the first food material is 400, the score of the second food material is 400×0.8=420, the score of the third food material is 400×0.6=240, the score of the fourth food material is 400×0.4=160, and the score of the fifth food material is 400×0.2=80.

The processor 110 calculates a necessary intake amount of each food material on the basis of the score for each food material calculated in the operation (S370). (S390)

In detail, the processor 110 calculates a necessary intake amount of each food material on the basis of the score for each food material calculated in the operation (S370), and can derive food material information for one dose of the analysis object.

Alternatively, the processor 110 calculates a necessary intake amount of each food material on the basis of the score for each food material calculated in the operation (S370), and can provide food material information by calculating the necessary intake amount by a specific weight unit (e.g., per 100 g).

Figure 9:
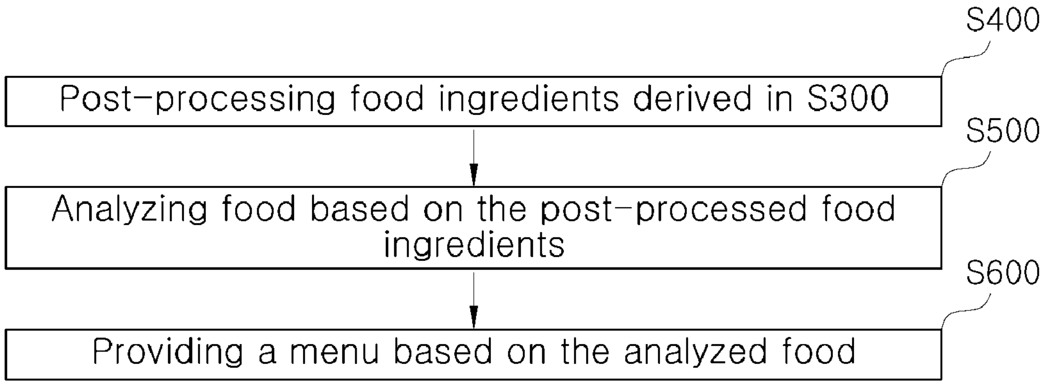
FIG. 9 is a view illustrating the next process after the food material deriving operation.

FIG. 9 is a view illustrating the next process after the food material deriving operation.

Referring to FIG. 9, the following operations may be further included after the food material deriving operation (S300).

The processor 110 proceeds to a post-processing process for the food material derived from the operation (S300). (S400)

The processor 110 analyzes the food based on the post-processed food material in the operation (S400). (S500)

The processor 110 provides a menu based on the food analyzed in the operation (S500). (S600)

In detail, the processor 110 performs post-processing process for the food material by performing at least one of filtering the food materials derived in the operation (S300) and deriving substitutional food materials to derive the final food material information.

The memory 150 stores at least one among a first exception condition predetermined, a second exception condition set for the analysis object, and a special weighted value set for a symptom or a disease.

The processor 110 may apply at least one among the first exception condition, the second exception condition, and the special weighted value to determine the type of the food material.

The first exception condition includes an acquisition difficulty of each food material.

In this instance, the acquisition difficulty may include an acquisition difficulty compared to the weight, a price per weight, and the like.

The second exception condition includes at least one among a food allergy and a food propensity of the analysis object.

The memory 150 stores substitutional food material information for a food material having an acquisition difficulty level equal to or higher than a predetermined difficulty level.

For example, in the case of a food material that is expensive or that is difficult to obtain in a user's country or location, the processor 110 can be replaced with a substitutional food material by filtering the food material.

When the acquisition difficulty level of the food material determined for the analysis object exceeds a preset difficulty level, the processor 110 may determine a substitutional food material set for the corresponding food material as a food material for the analysis object.

Figure 10:
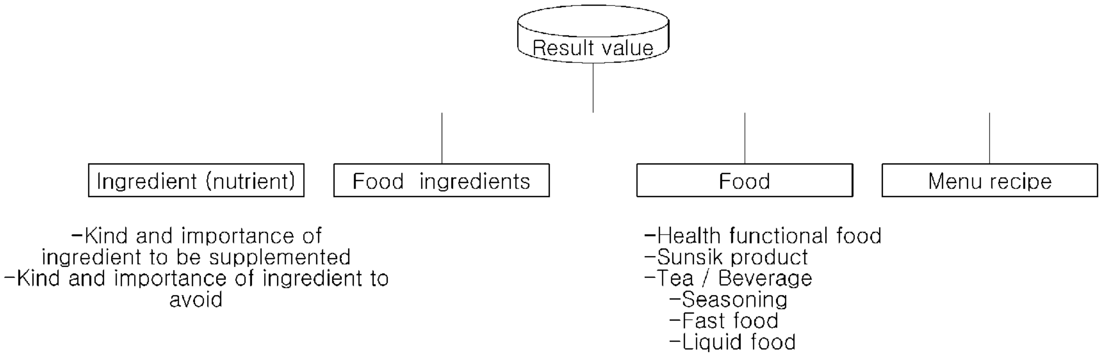
FIG. 10 is a view illustrating output data of the artificial intelligence-based food material analyzing method according to an embodiment of the present disclosure.

FIG. 10 is a view illustrating output data of the artificial intelligence-based food material analyzing method according to an embodiment of the present disclosure.

Referring to FIG. 10, the artificial intelligence-based food material analyzing method and system according to an embodiment of the present disclosure can provide information on the types and importance of ingredients to be supplemented for the analysis object, and provide the types and importance of ingredients to avoid.

In addition, the artificial intelligence-based food material analyzing method and system according to an embodiment of the present disclosure can provide a food material suitable for an analysis object, and provide food as well as a recipe of a menu.

In some embodiments, an artificial intelligence-based food material analyzing method may include: receiving, by a client terminal device, user information of a user; transmitting, by the client terminal device, to a service server device, the user information; requesting, by the service server device, to a medical staff terminal device, medical data corresponding to the user information; retrieving, by the medical staff terminal device, in a medical database, the medical data corresponding to the user information, wherein the medical data include information on inspection items and a plurality of hierarchy levels of the inspection items corresponding to the user information; transmitting, by the medical staff terminal device, the medical data to the service server device; generating, by the service server device, analysis input data including the user information and the medical data; inputting, by the service server device, the analysis input data to an artificial intelligence-based algorithm stored in a memory of the service server device, wherein the artificial intelligence-based algorithm performs: calculating ingredient power for each inspection item of the inspection items with respect to a first ingredient; calculating a first ingredient index that is a sum of ingredient powers for test items with respect to the first ingredient; deriving food material information based on the first ingredient index, from the food material database arranged based on ingredient contents; and outputting the derived food material information as a result value; an transmitting, from the service server device, the derived food material information to the client terminal device; and accessing, by the client terminal device, food material storage information, which indicates amounts of food materials stored in a food material storage of the user, and checking, by the client terminal device, whether an amount of an ingredient corresponding to the derived food material information, in the food material storage, exceeds a threshold level; in response to a detection that the amount of an ingredient corresponding to the derived food material information, in the food material storage, does not exceed the threshold level, generating and transmitting, by the client terminal device, a grocery order signal to a grocery delivery service server. The calculating the ingredient power may include: calculating a first weighted value corresponding to an importance of the inspection item, wherein the importance of the inspection item is based on a hierarchy level corresponding to the inspection item; calculating a second weighted value corresponding to a result value of the inspection item, wherein the result value is based on an input value of the inspection item for the user; calculating a third weighted value based on the second weighted value, wherein the third weighted value is based on output data of the inspection item for the user; and calculating the ingredient power by multiplying the first weighted value, the second weighted value, and the third weighted value.

In some embodiments, the client terminal device may be a smartphone, a portable personal computer, or a wearable device. The user information may be information identifying of a user. The service server device may be a server computer, a cloud service server computer, a data center computer, a smartphone, a portable personal computer, or a wearable device. The medical staff terminal device may be a personal computer, a smartphone, a portable personal computer, or a wearable device. The client terminal device, the service server device and the medical staff terminal device may be connected through one or more public or private networks, including the Internet, an Intranet, a WAN (Wide-Area Network), a MAN (Metropolitan-Area Network), a wireless network compliant with the IEEE 802.11a/b/g/n Standards, a leased line, or the like.

In some embodiments, the inspection items include at least one upper classification item, and the service server calculates the first weighted value by multiplying a classification weighted value set for the at least one upper classification item to which the inspection item belongs.

In some embodiments, the deriving the food material information comprises: correcting the calculated first ingredient index; setting a number of food material data extractions based on the corrected first ingredient index; extracting a same number of food materials as the number of food material data extractions; calculating scores of food materials by adding the corrected first ingredient index corresponding to each food material of the extracted food materials; and providing a necessary intake amount of the each food material based on the calculated scores.

In some embodiments, after the deriving the food material information, deriving final food material information by performing at least one of filtering the derived food material and deriving a substitutional food material may be performed.

In some embodiments, after deriving the final food material information, analyzing food corresponding to the derived final food material information; and providing a menu based on the analyzed food may be performed.

In some embodiments, identifying, by the service server device, ingredients for consisting the menu; and generating and transmitting, by the client terminal device, the grocery order signal to a grocery delivery service server, wherein the grocery order signal includes information on the identified ingredients may be performed.

In some embodiments, ingredients are something that enters as an element into a mixture: Flour, eggs, and sugar, and/or are any of the foods or substances that are combined to make a particular dish. The grocery delivery service server may be a server computer, a cloud service server computer, a data center computer, a smartphone, a portable personal computer, or a wearable device. The grocery delivery service server may access to a database configured to store information of a delivery location and of one or more grocery storage locations.

Figure 11:
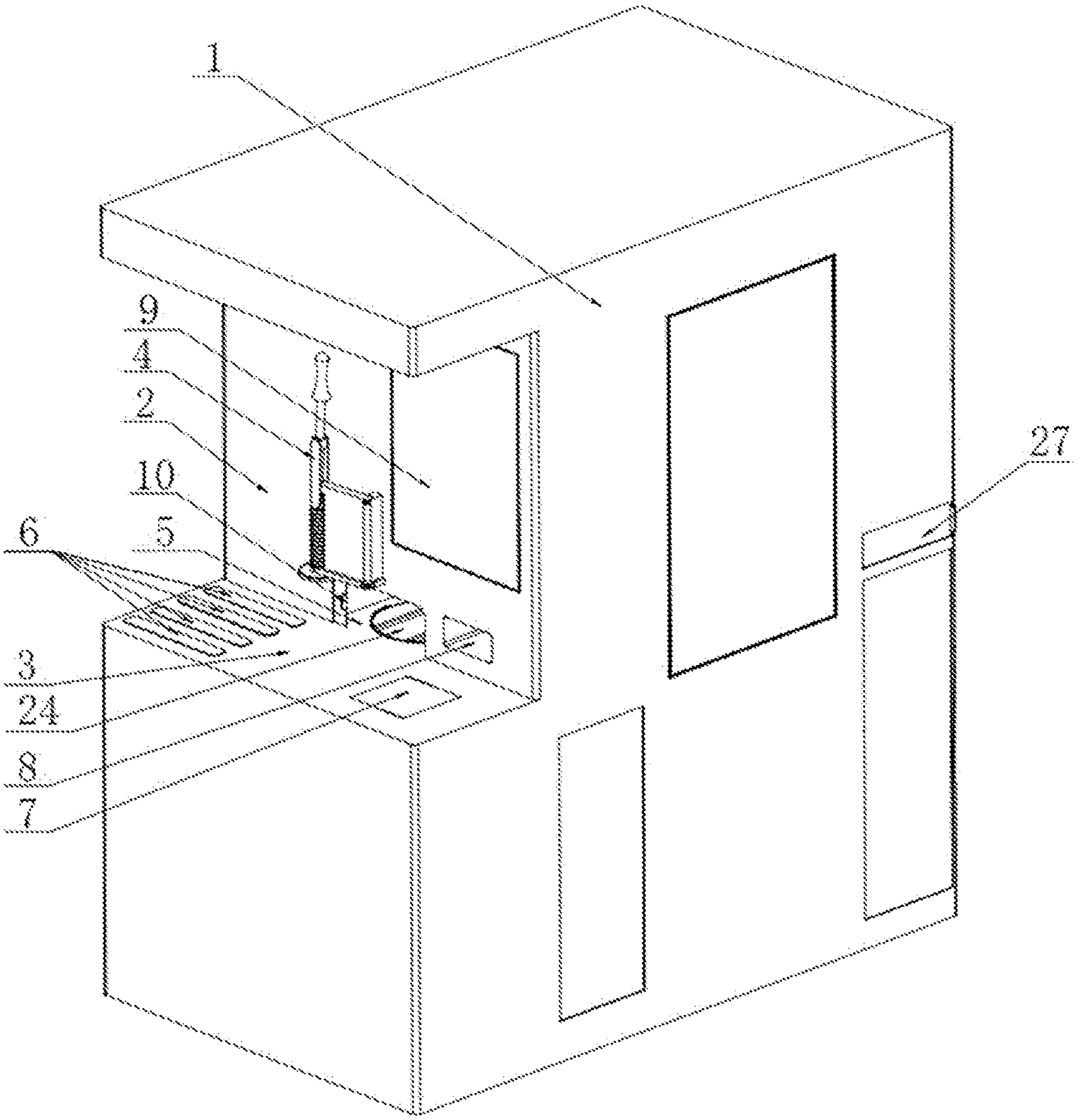
FIG. 11 a view illustrating an automated food preparation apparatus according to an embodiment of the present disclosure.

In some embodiments, when the client terminal device receives, from the grocery delivery service server, a signal indicating that a grocery order corresponding to the grocery order signal cannot be completed, mixing, by the client terminal device, ingredients stored in the food material storage to generate an additional food material corresponding to the derived food material information may be performed. In some embodiments, the client terminal device may access to a database having information regarding how to mix ingredients to generate an additional food material corresponding to the derived food material information. In some embodiments, the mixing operation can be performed by an automated food preparation apparatus, shown in FIG. 11. The automated food preparation apparatus 1 may include an exposed area 2, a manual operating table 3, a manual die press 4, a food exposing port 5, a tool storage rack 6, a material receiving box containing rack 7, a material receiving port 8, a touch screen 9, a sliding door 10, a forming station 24 and a meal outlet 27. The automated food preparation apparatus 1 may further include a robotic assembly, a mixing tank, a discharge mechanism, a displacement mechanism, an auxiliary material adding device, a chain, a rotary electric machine.

In some embodiments, an artificial intelligence-based food material analyzing service system may include a client terminal device including a processor and a memory, a service server device including a processor and a memory, a medical staff terminal device including a processor and a memory. The client terminal device is configured to: receive user information of a user; and transmit, to the service server device, the user information. The service server device is configured to: request, to the medical staff terminal device, medical data corresponding to the user information. The medical staff terminal device is configured to: retrieve, in a medical database, the medical data corresponding to the user information, wherein the medical data include information on inspection items and a plurality of hierarchy levels of the inspection items corresponding to the user information; and transmit the medical data to the service server device. The service server device is further configured to: generate analysis input data including the user information and the medical data; input the analysis input data to an artificial intelligence-based algorithm stored in the memory of the service server device, wherein the artificial intelligence-based algorithm performs: calculating ingredient power for each inspection item of the inspection items with respect to a first ingredient; calculating a first ingredient index that is a sum of ingredient powers for test items with respect to the first ingredient; deriving food material information based on the first ingredient index, from the food material database arranged based on ingredient contents; and outputting the derived food material information as a result value; and transmit the derived food material information to the client terminal device. The client terminal device is further configured to: access food material storage information, which indicates amounts of food materials stored in a food material storage of the user, and check whether an amount of an ingredient corresponding to the derived food material information, in the food material storage, exceeds a threshold level; in response to a detection that the amount of an ingredient corresponding to the derived food material information, in the food material storage, does not exceed the threshold level, generate and transmit a grocery order signal to a grocery delivery service server. The service server device is further configured to perform, in calculating the ingredient power: calculating a first weighted value corresponding to an importance of the inspection item, wherein the importance of the inspection item is based on a hierarchy level corresponding to the inspection item; calculating a second weighted value corresponding to a result value of the inspection item, wherein the result value is based on an input value of the inspection item for the user; calculating a third weighted value based on the second weighted value, wherein the third weighted value is based on output data of the inspection item for the user; and calculating the ingredient power by multiplying the first weighted value, the second weighted value, and the third weighted value.

In some embodiments, the inspection items include at least one upper classification item, and the service server device is further configured to calculate the first weighted value by multiplying a classification weighted value set for the at least one upper classification item to which the inspection item belongs.

In some embodiments, in deriving the food material information the service server device is further configured to: correct the calculated first ingredient index; set a number of food material data extractions based on the corrected first ingredient index; extract a same number of food materials as the number of food material data extractions; calculate scores of food materials by adding the corrected first ingredient index corresponding to each food material of the extracted food materials; and provide a necessary intake amount of the each food material based on the calculated scores.

In some embodiments, in deriving the food material information, the service server device is further configured to derive final food material information by performing at least one of filtering the derived food material and deriving a substitutional food material.

In some embodiments, after deriving the final food material information, the service server device is further configured to: analyze food corresponding to the derived final food material information; and provide a menu based on the analyzed food.

In some embodiments, the service server device is further configured to identify ingredients for consisting the menu, the client terminal device is further configured to generate and transmit the grocery order signal to a grocery delivery service server, and the grocery order signal includes information on the identified ingredients.

In some embodiments, when the client terminal device receives, from the grocery delivery service server, a signal indicating that a grocery order corresponding to the grocery order signal cannot be completed, the client terminal device is further configured to mix ingredients stored in the food material storage to generate an additional food material corresponding to the derived food material information.

In some embodiments, an artificial intelligence-based food material analyzing method may be performed by a service server comprising a processor and a memory storing a food material database. The method may include: receiving, from at least one of a client terminal and a medical staff terminal, by the service server, a food material analyzing service request for an analysis object including input data of the analysis object, wherein the input data includes information on inspection items and a plurality of hierarchy levels of the inspection items; in response to receiving the food material analyzing service request, performing of: accessing, by the service server, a server of an affiliated medical institution; receiving, from the server of the affiliated medical institution, by the service server, medical data for the analysis object; and automatically inputting, by the processor of the service server, the medical data to an artificial intelligence-based algorithm stored in the memory of the service server, wherein the artificial intelligence-based algorithm performs: calculating, by the processor of the service server, ingredient power for each inspection item of the inspection items with respect to a first ingredient; calculating, by the processor of the service server, a first ingredient index that is a sum of ingredient powers for test items with respect to the first ingredient; deriving, by the processor of the service server, food material information based on the first ingredient index, from the food material database arranged based on ingredient contents; and outputting, by the processor of the service server, the derived food material information as a result value; and transmitting, from the service server, the derived food material information to the client terminal. The calculating the ingredient power include: calculating a first weighted value corresponding to an importance of the inspection item, wherein the importance of the inspection item is based on a hierarchy level corresponding to the inspection item; calculating a second weighted value corresponding to a result value of the inspection item, wherein the result value is based on an input value of the inspection item for the analysis object; calculating a third weighted value based on the second weighted value, wherein the third weighted value is based on output data of the inspection item for the analysis object; and calculating the ingredient power by multiplying the first weighted value, the second weighted value, and the third weighted value.

In some embodiments, the inspection items include at least one upper classification item, and the service server calculates the first weighted value by multiplying a classification weighted value set for the at least one upper classification item to which the inspection item belongs.

In some embodiments, the deriving the food material information comprises: correcting the calculated first ingredient index; setting a number of food material data extractions based on the corrected first ingredient index; extracting a same number of food materials as the number of food material data extractions; calculating scores of food materials by adding the corrected first ingredient index corresponding to each food material of the extracted food materials; and providing a necessary intake amount of the each food material based on the calculated scores.

In some embodiments, after the deriving the food material information, deriving final food material information by performing at least one of filtering the derived food material and deriving a substitutional food material may be further performed.

In some embodiments, after deriving the final food material information, analyzing food corresponding to the derived final food material information; and providing a menu based on the analyzed food may be further performed.

In some embodiments, an artificial intelligence-based food material analyzing service server may include: a memory storing a weighted value calculation algorithm and a food material database; and a processor configured to: receive, from at least one of a client terminal and a medical staff terminal, a food material analyzing service request for an analysis object including input data of the analysis object, wherein the input data includes information on inspection items and a plurality of hierarchy levels of the inspection items; in response to the receipt of the food material analyzing service request, access a server of an affiliated medical institution, receive, from the server of the affiliated medical institution, medical data for the analysis object; and automatically input the medical data to an artificial intelligence-based algorithm stored in the memory, wherein the artificial intelligence-based algorithm is configured to: calculate ingredient power which calculates ingredient power for each inspection item of the inspection items with respect to a first ingredient; calculate a first ingredient index that is a sum of ingredient powers for test items with respect to the first ingredient; derive food material information based on the first ingredient index, from the food material database arranged based on ingredient contents; and output the derived food material information as a result value; and transmit the derived food material information to the client terminal. In calculating the ingredient power, the processor is further configured to: calculate a first weighted value corresponding to an importance of the inspection item, wherein the importance of the inspection item is based on a hierarchy level corresponding to the inspection item; calculate a second weighted value corresponding to a result value of the inspection item, wherein the result value is based on an input value of the inspection item for the analysis object; calculate a third weighted value based on the second weighted value, wherein the third weighted value is based on output data of the inspection item for the analysis object; and calculate the ingredient power by multiplying the first weighted value, the second weighted value, and the third weighted value.

In some embodiments, the inspection items include at least one upper classification item, and the processor is further configured to calculate the first weighted value by multiplying a classification weighted value set for the at least one upper classification item to which the inspection item belongs.

In some embodiments, in deriving the food material information, the processor is further configured to: correct the calculated first ingredient index; set a number of food material data extractions based on the corrected first ingredient index; extract a same number of food materials as the number of food material data extractions; calculate scores of food materials by adding the corrected first ingredient index corresponding to each food material of the extracted food materials; and provide a necessary intake amount of the each food material based on the calculated scores.

In some embodiments, in deriving the food material information, the processor is further configured to derive final food material information by performing at least one of filtering the derived food material and deriving a substitutional food material.

In some embodiments, after deriving the final food material information, the processor is further configured to: analyze food corresponding to the derived final food material information; and provide a menu based on the analyzed food.

In some embodiments, a non-transitory computer-readable recording medium of a service server may include a processor and a memory storing a food material database, the non-transitory computer-readable recording medium stores a program and is coupled with a computer hardware, and the program includes instructions to execute operations of: receiving, from at least one of a client terminal and a medical staff terminal, by the service server, a food material analyzing service request for an analysis object including input data of the analysis object, wherein the input data includes information on inspection items and a plurality of hierarchy levels of the inspection items; in response to receiving the food material analyzing service request, performing of: accessing, by the service server, a server of an affiliated medical institution; receiving, from the server of the affiliated medical institution, by the service server, medical data for the analysis object; and automatically inputting, by the processor of the service server, the medical data to an artificial intelligence-based algorithm stored in the memory of the service server, wherein the artificial intelligence-based algorithm performs: calculating, by the processor of the service server, ingredient power for each inspection item of the inspection items with respect to a first ingredient; calculating, by the processor of the service server, a first ingredient index that is a sum of ingredient powers for test items with respect to the first ingredient; deriving, by the processor of the service server, food material information based on the first ingredient index, from the food material database arranged based on ingredient contents; and outputting, by the processor of the service server, the derived food material information as a result value; and transmitting, from the service server, the derived food material information to the client terminal. The calculating the ingredient power may include: calculating a first weighted value corresponding to an importance of the inspection item, wherein the importance of the inspection item is based on a hierarchy level corresponding to the inspection item; calculating a second weighted value corresponding to a result value of the inspection item, wherein the result value is based on an input value of the inspection item for the analysis object; calculating a third weighted value based on the second weighted value, wherein the third weighted value is based on output data of the inspection item for the analysis object; and calculating the ingredient power by multiplying the first weighted value, the second weighted value, and the third weighted value.

The method according to an embodiment of the present disclosure can be implemented as a program (or application) to be executed by being combined with a server which is hardware, and can be stored in a medium.

In some embodiments, the aforementioned processes may be implemented as special-purpose hardware, such as a PLA, a PAL, a GAL, a CPLD, an FPGA, a SoC, or an ASIC. The aforementioned processes may be implemented as algorithms programmed into the special-purpose hardware that may perform the operations specified by the algorithms.

The program may include code coded as a computer language, such as C, C++, Java, machine language, etc. which a processor (CPU) of the computer can read through a device interface of a computer. The code may include a functional code associated with a function that defines necessary functions for executing the methods, and may include an execution procedure-related control code in which the processor of the computer needs to execute the functions according to predetermined procedures. In addition, the code may further include additional information necessary for the processor of the computer to execute the functions or memory reference-related code for whether the media should be referenced in which location (address) of the internal or external memory of the computer. Moreover, if communication with any other computer or server in a remote location is required to execute the functions by the process of the computer, the code may further include communication-related code for how to communicate with any other computer or server at a remote location using the communication module of the computer, or whether or not any information or media should be transmitted and received in the communication.

The medium to be stored refers not to a medium storing data for a short time but to a medium that stores data semi-permanently, like a register, cache, memory, and the like, and means a medium readable by a device. In detail, as examples of the medium to be stored, there are read-only memories (ROMs), random access memories (RAMs), CD-ROMs, magnetic tapes, floppy disks, optical data storage devices, and the likes, but the present disclosure is not limited thereto. That is, the program can be stored in various recording media on a variety of servers that can be accessed by a computer or various recording media on the user's computer. Furthermore, the media can store code that is distributed to a computer system connected to the network and that is readable by the computer in a distributed fashion.

The method or algorithm described in relation to the embodiments of the present disclosure can be directly embodied in hardware, can be embodied in a software module executed by hardware, or can be embodied by combination thereof. The software module can reside in a random access memory (RAM), a read-only memory (ROM), an erasable programmable read-only memory (EPROM), an electrically erasable programmable read-only memory (EEPROM), a flash memory, a hard disk, a detachable disk, a CD-ROM, or a medium readable by a computer, well-known in the technical field to which the present disclosure belongs.

The above description is only exemplary, and it will be understood by those skilled in the art that the disclosure may be embodied in other concrete forms without changing the technological scope and essential features. Therefore, the above-described embodiments should be considered only as examples in all aspects and not for purposes of limitation.

The invention claimed is:

1. An artificial intelligence-based food material analyzing method, comprising:

receiving, by a client terminal device, user information of a user;

transmitting, by the client terminal device, to a service server device, the user information;

requesting, by the service server device, to a medical staff terminal device, medical data corresponding to the user information;

retrieving, by the medical staff terminal device, in a medical database, the medical data corresponding to the user information, wherein the medical data include information on inspection items and a plurality of hierarchy levels of the inspection items corresponding to the user information;

transmitting, by the medical staff terminal device, the medical data to the service server device;

generating, by the service server device, analysis input data including the user information and the medical data;

inputting, by the service server device, the analysis input data to an artificial intelligence-based algorithm stored in a memory of the service server device, wherein the artificial intelligence-based algorithm performs:

calculating ingredient power for each inspection item of the inspection items with respect to a first ingredient;

calculating a first ingredient index that is a sum of ingredient powers for test items with respect to the first ingredient;

deriving food material information based on the first ingredient index, from the food material database arranged based on ingredient contents; and outputting the derived food material information as a result value; and transmitting, from the service server device, the derived food material information to the client terminal device; and accessing, by the client terminal device, food material storage information, which indicates amounts of food materials stored in a food material storage of the user, and checking, by the client terminal device, whether an amount of an ingredient corresponding to the derived food material information, in the food material storage, exceeds a threshold level;

in response to a detection that the amount of an ingredient corresponding to the derived food material information, in the food material storage, does not exceed the threshold level, generating and transmitting, by the client terminal device, a grocery order signal to a grocery delivery service server, wherein the calculating the ingredient power comprises:

calculating a first weighted value corresponding to an importance of the inspection item, wherein the importance of the inspection item is based on a hierarchy level corresponding to the inspection item;

calculating a second weighted value corresponding to a result value of the inspection item, wherein the result value is based on an input value of the inspection item for the user;

calculating a third weighted value based on the second weighted value, wherein the third weighted value is based on output data of the inspection item for the user; and calculating the ingredient power by multiplying the first weighted value, the second weighted value, and the third weighted value.

2. The method of claim 1, wherein the inspection items include at least one upper classification item, and wherein the service server calculates the first weighted value by multiplying a classification weighted value set for the at least one upper classification item to which the inspection item belongs.

3. The method of claim 1, wherein the deriving the food material information comprises:
correcting the calculated first ingredient index;
setting a number of food material data extractions based on the corrected first ingredient index;
extracting a same number of food materials as the number of food material data extractions;
calculating scores of food materials by adding the corrected first ingredient index corresponding to each food material of the extracted food materials; and
providing a necessary intake amount of the each food material based on the calculated scores.

4. The method of claim 1, after the deriving the food material information, further comprising:
deriving final food material information by performing at least one of filtering the derived food material and deriving a substitutional food material.

5. The method of claim 4, after deriving the final food material information, further comprising:
analyzing food corresponding to the derived final food material information; and
providing a menu based on the analyzed food.

6. The method of claim 5, further comprising:
identifying, by the service server device, ingredients for consisting the menu; and
generating and transmitting, by the client terminal device, the grocery order signal to a grocery delivery service server, wherein the grocery order signal includes information on the identified ingredients.

7. The method of claim 1, further comprising:
when the client terminal device receives, from the grocery delivery service server, a signal indicating that a grocery order corresponding to the grocery order signal cannot be completed, mixing, by the client terminal device, ingredients stored in the food material storage to generate an additional food material corresponding to the derived food material information.

8. An artificial intelligence-based food material analyzing service system, comprising:
a client terminal device including a processor and a memory;
a service server device including a processor and a memory;
a medical staff terminal device including a processor and a memory,
wherein the client terminal device is configured to:
receive user information of a user; and
transmit, to the service server device, the user information,
wherein the service server device is configured to:
request, to the medical staff terminal device, medical data corresponding to the user information,
wherein the medical staff terminal device is configured to:
retrieve, in a medical database, the medical data corresponding to the user information, wherein the medical data include information on inspection items and a plurality of hierarchy levels of the inspection items corresponding to the user information; and
transmit the medical data to the service server device,
wherein the service server device is further configured to:
generate analysis input data including the user information and the medical data;
input the analysis input data to an artificial intelligence-based algorithm stored in the memory of the service server device, wherein the artificial intelligence-based algorithm performs:
calculating ingredient power for each inspection item of the inspection items with respect to a first ingredient;
calculating a first ingredient index that is a sum of ingredient powers for test items with respect to the first ingredient;
deriving food material information based on the first ingredient index, from the food material database arranged based on ingredient contents; and
outputting the derived food material information as a result value; and
transmit the derived food material information to the client terminal device, wherein the client terminal device is further configured to:
access food material storage information, which indicates amounts of food materials stored in a food material storage of the user, and check whether an amount of an ingredient corresponding to the derived food material information, in the food material storage, exceeds a threshold level;
in response to a detection that the amount of an ingredient corresponding to the derived food material information, in the food material storage, does not exceed the threshold level, generate and transmit a grocery order signal to a grocery delivery service server,
wherein the service server device is further configured to perform, in calculating the ingredient power:
calculating a first weighted value corresponding to an importance of the inspection item, wherein the importance of the inspection item is based on a hierarchy level corresponding to the inspection item;
calculating a second weighted value corresponding to a result value of the inspection item, wherein the result value is based on an input value of the inspection item for the user;
calculating a third weighted value based on the second weighted value, wherein the third weighted value is based on output data of the inspection item for the user; and
calculating the ingredient power by multiplying the first weighted value, the second weighted value, and the third weighted value.

9. The system of claim 8, wherein the inspection items include at least one upper classification item, and
wherein the service server device is further configured to calculate the first weighted value by multiplying a classification weighted value set for the at least one upper classification item to which the inspection item belongs.

10. The system of claim 8, wherein in deriving the food material information the service server device is further configured to:
correct the calculated first ingredient index;
set a number of food material data extractions based on the corrected first ingredient index;
extract a same number of food materials as the number of food material data extractions;
calculate scores of food materials by adding the corrected first ingredient index corresponding to each food material of the extracted food materials; and
provide a necessary intake amount of the each food material based on the calculated scores.

11. The system of claim 8, wherein in deriving the food material information, the service server device is further configured to derive final food material information by performing at least one of filtering the derived food material and deriving a substitutional food material.

12. The system of claim 11, wherein after deriving the final food material information, the service server device is further configured to:

analyze food corresponding to the derived final food material information; and provide a menu based on the analyzed food.

13. The system of claim 12, wherein the service server device is further configured to identify ingredients for consisting the menu, wherein the client terminal device is further configured to generate and transmit the grocery order signal to a grocery delivery service server, and wherein the grocery order signal includes information on the identified ingredients.

14. The system of claim 8, further comprising:

when the client terminal device receives, from the grocery delivery service server, a signal indicating that a grocery order corresponding to the grocery order signal cannot be completed, the client terminal device is further configured to mix ingredients stored in the food material storage to generate an additional food material corresponding to the derived food material information.

* * * * *